US009296981B2

(12) United States Patent
Matthews et al.

(10) Patent No.: US 9,296,981 B2
(45) Date of Patent: Mar. 29, 2016

(54) REMOVAL OF BACTERIAL ENDOTOXINS

(75) Inventors: Michael A. Matthews, Columbia, SC (US); Pedro J. Tarafa, Ponce, PR (US)

(73) Assignee: University of South Carolina, Columbia, SC (US)

( * ) Notice: Subject to any disclaimer, the term of this patent is extended or adjusted under 35 U.S.C. 154(b) by 680 days.

(21) Appl. No.: 13/197,261

(22) Filed: Aug. 3, 2011

(65) Prior Publication Data

US 2012/0035089 A1 Feb. 9, 2012

Related U.S. Application Data

(60) Provisional application No. 61/400,849, filed on Aug. 3, 2010.

(51) Int. Cl.

| | |
|---|---|
| ***C11D 1/00*** | (2006.01) |
| ***B08B 3/04*** | (2006.01) |
| ***A61L 2/16*** | (2006.01) |
| ***C11D 17/00*** | (2006.01) |
| ***C11D 3/02*** | (2006.01) |

(52) U.S. Cl.

CPC .............. *C11D 17/0021* (2013.01); *C11D 3/02* (2013.01)

(58) Field of Classification Search

CPC .......... C11D 1/00; B08B 3/04; A61L 2/0082; A61L 2/16

USPC .......... 422/28; 510/161, 421, 505; 134/22.11, 134/22.12, 22.14, 22.18, 39, 42

See application file for complete search history.

(56) References Cited

U.S. PATENT DOCUMENTS

| | | | | |
|---|---|---|---|---|
| 6,235,701 | B1 * | 5/2001 | Senger Elsbernd | 510/412 |
| 6,491,231 | B1 | 12/2002 | Eliasson et al. | |
| 6,966,144 | B2 | 11/2005 | Eliasson et al. | |
| 7,293,570 | B2 | 11/2007 | Jackson | |
| 2004/0033269 | A1 * | 2/2004 | Hei et al. | 424/616 |
| 2005/0054702 | A1 | 3/2005 | Dunn et al. | |
| 2005/0156065 | A1 | 7/2005 | Eliasson | |
| 2005/0227897 | A1 | 10/2005 | Nelson et al. | |

FOREIGN PATENT DOCUMENTS

| | | |
|---|---|---|
| WO | 2003090805 | 11/2003 |

OTHER PUBLICATIONS

An et al., "Effects of sterilization on implant mechanical property and biocompatibility—A concise review". International Journal of Artificial Organs 2005, 28, 1126-1137.

Ballestra et al., "Inactivation of *Escherichia coli* by carbon dioxide under pressure". Journal of Food Science 1996, 61, 829-831, 836.

Ballestra et al., "Influence of pressurized carbon dioxide on the thermal inactivation of bacterial and fungal spores". Lebensmittel-Wissenschaft und—Technologie 1998, 31, 84-88.

(Continued)

*Primary Examiner* — Brian P Mruk

(57) ABSTRACT

Methods of cleaning a medical device are provided via exposing the medical device to a compressed $CO_2$-based mixture. The compressed $CO_2$-based mixture includes carbon dioxide, a surfactant, and water in the form of water-in-$CO_2$ microemulsions. In one particular embodiment, the ratio of water-to-surfactant mixed together in the $CO_2$ has a range of about 5-100 molecules of water per molecule of surfactant (e.g., about 5-30 molecules of water per molecule of surfactant).

20 Claims, 9 Drawing Sheets

(56) References Cited

OTHER PUBLICATIONS

Bell et al. "Biomedical membranes from hydrogels and interpolymer complexes". Advances in Polymer Science 1995, 122, 125-175.
Cappuccino et al. Microbiology a Laboratory Manual 2001, 123.
Collier et al. "Comparison of cross-linked polyethylene materials for orthopaedic applications". Clinical orthopaedics and related research 2003, 414, 289-304.
Costa et al. "Invivo UHMWPE biodegradation of retrieved prosthesis". Biomaterials 1998, 19, 1371-1385.
Debs-Louka et al. "Effect of compressed carbon dioxide on microbial cell viability". Applied and Environmental Microbiology 1999, 65, 626-631.
Dillow et al. "Bacterial inactivation by using near- and supercritical carbon dioxide". Proceedings of the National Academy of Sciences of the United States of America 1999, 96, 10344-10348.
Elvassore et al. "Micro-organisms inactivation by supercritical CO2 in a semi-continuous process". In: Perrut M, Reverchon E, editors; Dec. 6-8, 2000; Antibes (France). p. 773-778.
Enomoto et al. "Inactivation of food microorganisms by high-pressure carbon dioxide treatment with or without explosive decompression". Bioscience Biotechnology and Biochemistry 1997, 61, 1133-1137.
Erkmen, O. "Antimicrobial effect of pressurized carbon dioxide on *Staphylococcus aureus* in broth and milk". Food Science & Technology (London) 1997, 30, 826-829.
Erkmen, O. "Effect of carbon dioxide pressure on Listeria monocytogenes in physiological saline and foods". Food Microbiology 2000, 17, 589-596.
Erkmen, O. "Inactivation of *Salmonella typhimurium* by high pressure carbon dioxide". Food Microbiology 2000, 17, 225-232.
Erkmen, O. "Effects of high-pressure carbon dioxide on *Escherichia coli* in nutrient broth and milk". International Journal of Food Microbiology 2001, 65, 131-135.
Erkmen, O. "Kinetic analysis of Listeria monocytogenes inactivation by high pressure carbon dioxide". Journal of Food Engineering 2001, 42, 7-10.
Farewell et al. "Effect of temperature on in vivo protein synthetic capacity in *Escherichia coli*". Journal of Bacteriology 1998, 180, 4704-4710.
Galas et al. "Humidity-conditioned gravimetric method to measure the water content of hydrogel contact lens materials". Optometry and Vision Science: Official Publication of the American Academy of Optometry 1993, 70, 577-586.
Ghandehari et al. "In vitro degradation of pH-sensitive hydrogels containing aromatic azo bonds". Biomaterials 1997, 18, 861-872.
Hong et al. "Non-thermal inactivation of Lactobacillus plantarum as influenced by pressure and temperature of pressurized carbon dioxide". International Journal of Food Science and Technology 1999, 34, 125-130.
Ishikawa et al. "Inactivation of Bacillus spores by the supercritical carbon dioxide micro-bubble method". Bioscience, Biotechnology, and Biochemistry 1997, 61, 1022-1023.
Jimenez et al. Evaluation of CO2—Based Cold Sterilization of a Model Hydrogel. Biotech Bioeng., 101(6), 1344-1352, 2008.
Kamihira et al. "Sterilization of microorganisms with supercritical carbon dioxide". Agricultural and Biological Chemistry 1987, 51, 407-12.
Kishida et al. "Hydrogels for biomedical and pharmaceutical applications". Polymeric Biomaterials (2nd Edition) 2002, 133-145.
Koros et al. "High-pressure sorption of carbon dioxide in solvent-cast poly(methyl methacrylate) and poly(ethyl methacrylate) films". Journal of Applied Polymer Science 1981, 26, 159-170.
Lee et al. "Synthesis and characteristics of interpenetrating polymer network hydrogel composed of chitosan and poly(acrylic acid)". Journal of Applied Polymer Science 1999, 73, 113-120.
Lopatin et al. "Structure and relaxation properties of medical-purposed polyacrylamide gels". Journal of Applied Polymer Science 2005, 96, 1043-1058.
McHugh et al. "Supercritical Fluid Extraction". Newton, MA: Butterworth-Heinemann. 1994, 1-16 p.
Park GB. "Burn wound coverings—a review". Biomaterials, Medical Devices, and Artificial Organs 1978, 6, 1-35.
Ruel-Gariepy et al. "Thermosensitive chitosan-based hydrogel containing liposomes for the delivery of hydrophilic molecules". Journal of Controlled Release 2002, 82, 373-383.
Sawan et al. "Evaluation of the Interactions Between Supercritical Carbon Dioxide and Polymeric Materials". Lowell, MA: Los Alamos National Laboratory. 1995, 7-32 p.
Schmidt et al. "Disinfection of textile materials contaminated with *E. coli* in liquid carbon dioxide". Journal of Cleaner Production 2005, 13, 881.
Span et al. "A new equation of state for carbon dioxide covering the fluid region from the triple-point temperature to 1100 K at pressures up to 800 MPa". Journal of Physical and Chemical Reference Data 1996, 25, 1509-1596.
Spilimbergo et al. "Non-thermal bacterial inactivation with dense CO2". Biotechnology and Bioengineering 2003, 84, 627-638.
Stockar, U. "Effect of a near-critical and supercritical fluid on the viability ratio of microbial cells". Progress in Biotechnology 1992, 8, 407-416.
White et al. "Effective terminal sterilization using supercritical carbon dioxide". Journal of Biotechnology 2006, 123, 504-515.
Wu et al. "Influence of the COOH and COONa groups and crosslink density of poly(acrylic acid)/montmorilionite superabsorbent composite on water absorbency". Polymer International 2001, 50, 1050-1053.
Zhang et al. "Synthesis and Properties of Sepiolite/poly(acryilc acid-co-acrylamide) Nanocomposites". Polymer Bulletin 2005, 55, 419-428.
Zhang et al. "On the mechanisms of deactivation of Bacillus atrophaeus spores using supercritical carbon dioxide". Journal of Supercritical Fluids 2006 38, 268-273.
Andrews et al. "Effects of sterilisation method on surface topography and in-vitro cell behaviour of electrostatically spun scaffolds." Biomaterials 2007, 28, 1014-1026.
Athanasiou et al. "Sterilization, toxicity, biocompatibility and clinical applications of polylactic acid/ polyglycolic acid copolymers." Biomaterials 1996, 17, 93-102.
Carrascosa et al. "Effect of gamma-sterilization process on PLGA microspheres loaded with insulin-like growth factor-I (IGF-I)." Journal of Biomaterials Applications 2003, 18, 95-108.
Desai et al. "Study of Gamma-Irradiation Effects on Chitosan Microparticles." Drug Delivery 2006, 13, 39-50.
Draganic et al. "Formation of primary yields of hydroxyl radical and hydrated electron in the gamma-radiolysis of water." J. Phys. Chem. 1973, 77, 765-772.
Fischbach et al. "Does UV irradiation affect polymer properties relevant to tissue engineering?" Surface Science 2001, 491, 333-345.
Gogolewski et al. "Sterility, mechanical properties, and molecular stability of polylactide internal-fixation devices treated with low-temperature plasmas." Journal of Biomedical Materials Research 1996, 32, 227-235.
Grimes et al. "The effect of choice of sterilisation method on the biocompatibility and biodegradability of SIS (small intestinal submucosa)." Bio-Medical Materials & Engineering 2005, 15, 65-71.
Hemmer et al. "Sterilization of Bacterial Spores by Using Supercritical Carbon Dioxide and Hydrogen Peroxide." Journal of Biomedical Material Research (Part B) 2007, 80, 511-518.
Holy et al. "Optimizing the sterilization of PLGA scaffolds for use in tissue engineering." Biomaterials 2001, 22, 25-31.
Huebsch et al. "Analysis of sterilization protocols for peptide-modified hydrogels." Journal of Biomedical Materials Research (Part B) 2005, 74, 440-447.
Kato et al. "Oxidative degradation of collagen and its model peptide by ultraviolet irradiation." J. Agric. Food Chem. 1992, 40, 373-379.
Kelly-Wintenberg et al. "Use of a one atmosphere uniform glow discharge plasma to kill a broad spectrum of microorganisms." Journal of Vacuum Science & Technology a-Vacuum Surfaces and Films 1999, 17, 1539-1544.

(56) References Cited

OTHER PUBLICATIONS

Lerouge et al. "Plasma Sterilization: A Review of Parameters, Mechanisms, and Limitations." Plasmas and Polymers 2001, 6, 175-188.
Majewski et al. "Effects of ultraviolet radiation on the type-I collagen protein triple helical structure: A method for measuring structural changes through optical activity." Physical Review E 2002, 65, 031920.
Markowitz et al. "The impact of vacuum freeze-drying on collagen sponges after gas plasma sterilization." Journal of Biomaterials Science 2006, 17, 61-75.
Moioli et al. "Sustained Release of TGFβ3 from PLGA Microspheres and Its Effect on Early Osteogenic Differentiation of Human Mesenchymal Stem Cells." Tissue Engineering 2006, 12, 537-546.
Nair. "Currently practised sterilization methods—some inadvertent consequences." Journal of Biomaterials Applications 1995 10, 121-135.
Noah et al. "Impact of sterilization on the porous design and cell behavior in collagen sponges prepared for tissue engineering." Biomaterials 2002, 23, 2855-2861.
O'Leary et al. "The toxicogenic potential of medical plastics sterilized with ethylene oxide vapors." Journal of Biomedical Materials Research 1968, 2, 297-311.
Ozalp et al. "Controlled release of vancomycin from biodegradable microcapsules." Journal of Microencapsulation 2001, 18, 89-110.
Rutala et al. "Comparative evaluation of the sporicidal activity of new low-temperature sterilization technologies: ethylene oxide, 2 plasma sterilization systems, and liquid peracetic acid." American Journal of Infection Control 1998, 26, 393-398.
Shearer et al. "Effects of Common Sterilization Methods on the Structure and Properties of Poly (D,L Lactic-Co-Glycolic Acid) Scaffolds." Tissue Engineering 2006, 12, 2717-2727.
Zhang et al. "Supercritical carbon dioxide and hydrogen peroxide cause mild changes in spore structures associated with high killing rate." Journal of Microbiological Methods 2007, 70, 442-451.
Casas et al. "Effect of addition of cosolvent on the supercritical fluid extraction of bioactive compounds from *Helianthus annuus* L." Journal of Supercritical Fluids 2007, 41, 43-49.
Charlton et al. "A comparison of the efficacy of lumen-cleaning devices for flexible gastrointestinal endoscopes." Australian Infection Control 2007, 12, 81-90.
Cholvin et al. "General compatibility". Handbook of biomaterials evaluation: Scientific, technical, and clinical testing of implant materials, $2^{nd}$ edition, 1998, 507-522.
Ding et al. "A new era in pyrogen testing." Trends in Biotechnology 2001, 19, 277-281.
Donlan. "Biofilms and device-associated infections." Emerging Infectious Diseases 2001, 7, 277-281.
Fitzgerald. "Infections of hip prostheses and artificial joints." Infectious Disease Clinics of North America 1989, 3, 329-338.
Gagnon et al. "Endotoxin affinity for provisional restorative resins." Journal of Prosthodontics 1994, 3, 228-236.
Gorbet et al. "Endotoxin: The uninvited guest." Biomaterials 2005, 26, 6811-6817.
Granados et al. "Assessment of parameters associated to the risk of PVC catheter reuse." J Biomed Mater Res 2001, 58, 505-510.
Hagman. "Sterilization." Remington: The science and practice of pharmacy 2005, 776-801.
Heinrich et al. "Endotoxin in fine($PM_{2.5}$) and coarse ($PM_{2.5-10}$) particle mass of ambient aerosols: A temporal-spatial analysis." Atmospheric Environment 2003, 37, 3659-3667.
Joslyn. "Sterilization by heat". Disinfection, sterilization, and preservation, $3^{rd}$ edition, 1983, 27-30, 766-767.
King et al. "The mutual solubilities of water with supercritical and liquid carbon dioxide." Journal of Supercritical Fluids 1992, 5, 296-302.
Knoernschild et al. "Endotoxin adherence to and elution from two casting alloys." The International Journal of Prosthodontics 1994, 7, 22-29.
Kundsin et al. "Detection of Endotoxin on Sterile Catheters Used for Cardiac Catheterization." Journal of Clinical Microbiology 1980, 11, 209-212.
Liu et al. Formation of Water-in-$CO_2$ Microemulsions with Non-fluorous Surfactant Ls-54 and Solubilization of Biomacromolecules. Chem Eur J 2002, 8, 1356-1360.
Martich et al. "Response of man to endotoxin." Immunobiology 1993, 187, 403-416.
Morrison et al. "Current status of bacterial endotoxins." ASM News 1994, 60, 479-484.
Nakagawa et al. "Endotoxin contamination in wound dressings made of natural biomaterials." J Biomed Mater Res 2003, 66, 347-355.
Nelson et al. "Lipopolysacharide affinity for titanium implant biomaterials." The Journal of Prosthetic Dentistry 1997, 77, 76-82.
Novitsky et al. "Factors affecting recovery of endotoxin adsorbed to container surfaces." Journal of Parenteral Science and Technology 1986, 40, 284-286.
Ohno et al. "Lipopolysaccharide interaction with lysozyme: Binding of lipopolysaccharide to lysozyme and inhibition of lysozyme enzymatic activity." The Journal of Biological Chemistry 1989, 264, 4434-4441.
Pabst et al. "Bacterial LPS: A mediator of inflammation." Handbook of Inflammation 1989, 361-393.
Park et al. "Predictors of airborne endotoxin in the home." Environmental Health Perspectives 2001, 109, 859-864.
Raetz. "Biochemistry of endotoxins." Annual Review of Biochemistry 1990, 59, 129-170.
Ragab et al. "Measurement and removal of adherent endotoxin from titanium particles and implant surfaces." J Orthop Res 1999, 17, 803-809.
Ramakrishna. "Safety of technology: Infection control standards in endoscopy." Journal of Gastroenterology and Hepatology 2002, 17, 361-368.
Reyes et al. "Pyrogenic reactions after inadvertent infusion of endotoxin during cardiac catheterizations." Annals of Internal Medicine 1980, 93, 32-55.
Rietschel et al. "Bacterial endotoxins." Scientific American 1992, 267, 54-61.
Rietschel et al. "Bacterial endotoxin: molecular relationship of structure to function." The FASEB Journal 1994, 8, 217-225.
Rioufol et al. "Quantitative determination of endotoxins released by bacterial biofilms." Journal of Hospital Infection 1999, 43, 203-209.
Robinson et al. "*Porphyromonas gingivalis* endotoxin affinity for dental ceramics." Journal of Prosthetic Dentistry 1996, 75, 217-227.
Rudnick et al. "An outbreak of pyrogenic reactions in chronic hemodialysis patients associated with hemodialyzer reuse." Artif Organs 1995, 19, 289-294.
Rutala et al. Reprocessing endoscopes: United Stated perspective. Journal of Hospital Infection 2004, 56, 27-39.
Sweadner et al. "Filtration removal of endotoxin (pyrogens) in solution in different state of aggregation." Applied and Environment Microbiology 1977, 34,382-385.
Tessarolo et al. "Efficiency in endotoxin removal by a reprocessing protocol for electrophysiology catheters based on hydrogen peroxide plasma sterilization." International Journal of Hygiene and Environmental Health 2006, 209, 557-565.
Tsuji et al. "Dry heat destruction of LPS: Drug heat destruction kinetics." Applied and Environment Microbiology 1978, 36, 710-714.
Weary et al. "A manufacturer's guide to depyrogenation." BioPharm Manuf 1988, 1, 22-29.
M. Belton, "Allergen impermeable covers appear clinically ineffective in the management of adult asthma patients." N Engl J. Med. 2003, 349, 3.
Bischoff et al., "Assessment of mite numbers: new methods and results." Experimental & Applied Acarology 1992, 16, 1-14.
de Boer et al., "The decay of house dust mite allergens, Der p I and Der p II, under natural conditions." Clin Exp Allergy 1995, 25, 765-770.
Eastoe et al., "Self-assembly in green solvents". Physical Chemistry Chemical Physics 2005, 7, 1352-1362.

(56) References Cited

OTHER PUBLICATIONS

Ginty et al., "Mammalian cell survival and processing in supercritical $CO_2$"-Proceedings of the National Academy of Sciences 2006, 103, 7426-7431.
John et al., "Functional effects of the inhibition of the cysteine protease activity of the major house dust mite allergen der p 1 by a novel peptide-based inhibitor". Clinical and Experimental Allergy 200, 30, 784-793.
Jovanovic et al., "Stabilization of proteins in dry powder formulations using supercritical fluid technology". Pharmaceutical Research 2004, 21, 1955-69.
Kauffman et al., "House dust mite major allergens Der p 1 and Der p 5 activate human airway-derived epithelial cells by protease-dependent and protease-independent mechanisms." Clinical and Molecular Allergy 2006, 4:5.
Kawamoto et al., "Toward elucidating the full spectrum of mite allergens—state of the art." Journal of Bioscience and Bioengineering 2002, 94, 285-298.
Kort et al., "Four-year stability of Der p I in house dust under simulated domestic conditions in vitro." Allergy 1994, 49, 131-133.
Lau et al., "Placebo-controlled study of the mite allergen-reducing effect of tannic acid plus benzyl benzoate on carpets in homes of children with house dust mite sensitization and asthma." Pediatric Allergy and Immunology 2002, 13, 31-36.
Sidenius et al., "Decay of house-dust mite allergen Der f 1 at indoor climatic conditions." Annals of Allergy, Asthma & Immunology 2002, 89, 34-37.
Woodcock et al., "Control of Exposure to Mite Allergen and Allergen-Impermeable Bed Covers for Adults with Asthma." N Engl J Med 2003, 349, 225-236.
Zagrobelny et al., "In situ studies of protein conformation in supercritical fluids: Trypsin in carbon dioxide". Biotechnology Progress 1992, 8, 421-423.
Zhang et al., "Sterilizing *Bacillus pumilus* spores using supercritical carbon dioxide". Journal of Microbiological Methods 2006, 66, 479-485.
Zhang et al., "Sterilization using high-pressure carbon dioxide". Journal of Supercritical Fluids 2006, 38, 354-372.
Matthews et al., U.S. Appl. No. 13/235,807, filed Sep. 19, 2011, Methods and Compositions for Dislodging Debris Particles from a Substrate.
Matthews et al., U.S. Appl. No. 13/074,220, filed Mar. 29, 2011, Cold Sterilization of Tissue Engineering Scaffolds with Compressed Carbon Dioxide.
Matthews et al., U.S. Appl. No. 13/070,845, filed Mar. 24, 2011, Removal of Bacterial Endotoxins.

* cited by examiner

REMOVAL OF BACTERIAL ENDOTOXINS

PRIORITY INFORMATION

The present application claims priority to U.S. Provisional Patent Application Ser. No. 61/400,849 filed on Aug. 3, 2010 of Matthews, et al. titled "Removal of Bacterial Endotoxins," the disclosure of which is incorporated by reference herein.

GOVERNMENT SUPPORT CLAUSE

This invention was made with government support under R01EB55201 awarded by National Institutes of Health. The government has certain rights in the invention.

BACKGROUND OF THE INVENTION

Most common cleaning methods for reusable medical devices and biomaterials rely on manual and automated washing, using brushes to dislodge soil in the presence of water and detergents, or organic solvents. However, the cleaning apparatus may compound the accumulation of residual soil by causing surface abrasion or grooving. Failure to successfully clean the medical device leads to biofilm formation and bacterial colonization, which may harbor bacterial residuals such as endotoxins.

Endotoxin contamination and its effects on biocompatibility have not yet entered into widespread consciousness among biomaterial specialists. Endotoxins, also called lipopolysacharides (LPS), are an integral part of the outer cell membrane of Gram-negative bacteria that are shed upon cell death, growth, and division. When introduced to the blood stream, they elicit an immune response, especially through monocytes and macrophages. These cells release mediators, such as tumor necrosis factor and free radicals, having potent biological activity responsible for adverse effects. Among these are affecting structure and function of organ cells, changing metabolic functions, raising body temperature (pyrogen reactions) triggering the coagulation cascade, modifying hemodynamics, causing septic shock, and in extreme cases multiple organ failure, with a high mortality rate.

Due to their ubiquitous nature, endotoxins are persistent bio-contaminants that deposit and adhere to many materials. Previous studies have revealed that significant levels (15 endotoxin units (EU)/$m^2$ of surface area) of adherent endotoxin existed on cleaned, passivated, and gamma-sterilized implant surfaces, especially on those made from titanium (Ti). Their ability to adhere to materials has been related to many factors such as material type, surface properties, and pH. However, affinity for metallic biomaterials such as Ti appears to be primarily a function of surface energy. The surface energy of the endotoxins is thought to be about 30 mJ/$m^2$ or less. Hence, for endotoxins to adhere, the biomaterial must exhibit surface energies greater than 30 mJ/$m^2$.

Eliminating endotoxins has been a major challenge to the pharmaceutical and medical industry, and is by far the greatest concern in achieving depyrogenation of medical devices. Yet, a generally applicable method for the removal of endotoxins is not available. Since endotoxins are highly heat-stable they are not destroyed by standard autoclaving conditions. However, endotoxins can be destroyed by dry heat at 250° C. for more than 30 min or at 180° C. for more than 3 h. However, there are possible complications associated with dry-heat decontamination. One is the lack of uniformity of temperature within the oven. Hot air has a tendency to stratify and may not uniformly heat a cooler material. Another complication is heat damage and oxidation of biomaterials. To remove endotoxin from metallic particles a cycle of alkali ethanol (0.1 M NaOH in 95% ethanol) at 30° C. followed by 25% nitric acid both for 18-20 h each is recommended. In reusable medical devices, a useful recommendation to minimize endotoxin contamination is to process, package, and promptly sterilize the item in order to limit the time of bacterial contamination and growth. However, conventional sterilization by steam or ethylene oxide does not destroy endotoxin, and does not alter the pyrogenic activity of endotoxic fragments.

Thus, a need still remains for techniques and processes to achieve safe endotoxin levels on medical devices (e.g., ≤20 EU/device according to the US Pharmacopeia-Standard USP27-NF22).

SUMMARY

Objects and advantages of the invention will be set forth in part in the following description, or may be obvious from the description, or may be learned through practice of the invention.

Methods of cleaning a medical device are generally provided via exposing the medical device to a compressed $CO_2$-based mixture. The compressed $CO_2$-based mixture includes carbon dioxide, a surfactant, and water in the form of water-in-$CO_2$ microemulsions. In one particular embodiment, the ratio of water-to-surfactant mixed together in the $CO_2$ has a range of about 5-100 molecules of water per molecule of surfactant (e.g., about 5-30 molecules of water per molecule of surfactant).

The compressed $CO_2$-based mixture can have a temperature of about 0° to about 100° C. (20° C. to about 60° C.) and a pressure of at least about 400 psi (e.g., about 400 to about 600 psi or about 800 to about 5000 psi). As such, the compressed $CO_2$-based mixture can be a liquid or a super critical fluid, depending on the temperature and pressure selected.

According to certain embodiments, the compressed $CO_2$-based mixture can remove at least 85% of bacterial endotoxin from the medical device, such as at least 95% of bacterial endotoxin from the medical device. In one particular embodiment, the compressed $CO_2$-based mixture can remove at least 99% of bacterial endotoxin from the medical device.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

DETAILED DESCRIPTION OF INVENTION

Figure 1:
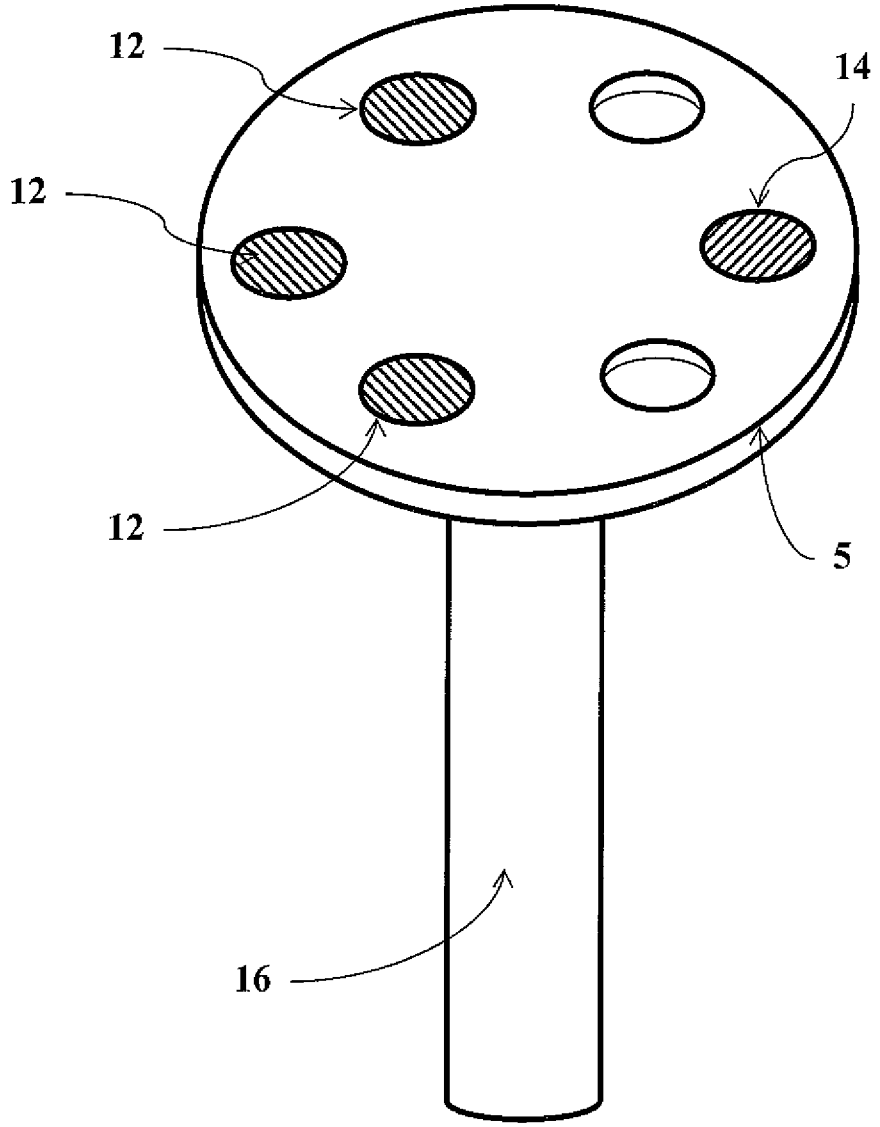
FIG. 1 shows a stainless steel plate with Ti disks, according to the Examples.

The following description and other modifications and variations to the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the following description is by way of example only, and is not intended to limit the invention.

Generally speaking, the present invention is directed towards a process that will substantially remove bacterial endotoxins from biomaterials and reusable medical devices. In particular, methods for the removal of bacterial endotoxins (e.g., *Escherichia coli*) are provided through the use of compressed carbon dioxide ($CO_2$)-based mixtures.

To enhance the water solubility in $CO_2$ and make it accessible for dissolving endotoxins, a surfactant can be used to form water-in-$CO_2$ microemulsions. A microemulsion is a thermodynamically stable dispersion of two immiscible fluids stabilized by surfactants. There are roughly three types of microemulsions; water-in-oil, bicontinuous, and oil-in-water microemulsions. Surfactants typically have very low volatility, and thus interact to a much lesser degree with the substrate. Furthermore, they often dramatically improve the solubility of polar species, well beyond that of simple modifiers.

Microemulsions containing water, surfactant and, $CO_2$ have been designed to achieve: (1) low interfacial tensions for favorable wetting of small features on substrate; (2) solubilization of residues into micelles in water, water droplets, or $CO_2$ continuous phase; and (3) prevention of redeposition. The advantages of using compressed $CO_2$ as the continuous phase over conventional organic solvents for cleaning are that, in addition to being nontoxic and nonflammable, $CO_2$ has low viscosity and high diffusion coefficient. Moreover, the stability of water-in-$CO_2$ microemulsions depends on the density of the compressed $CO_2$. Therefore, the breakdown of the microemulsions can be accomplished simply by controlling the temperature and/or pressure of the system. The temperature range for $CO_2$-based systems is typically 0° to 100° C., (e.g., about 20° C. to about 60° C.).

A $CO_2$-based microemulsion would have minimal environmental impact since, at this scale of use, the solvent is environmentally benign. In addition, the $CO_2$ continuous phase has a very high capacity for lower polarity organic solutes, and these materials can be easily recovered from the solvent. The very high transport rates of the SCF phase (at least an order of magnitude higher than for water) greatly enhance the cleaning rates and are especially attractive for processing of porous or intricate materials. Finally, the polarity of the $CO_2$ microemulsion can be adjusted either through selection of different types of surfactants or through adjustments in the amount of water that is added to the microemulsion. The ability of the microemulsion to dissolve polar solutes depends solely on the characteristic of the microemulsion droplet. Thus, the design of surfactants compatible with $CO_2$ is crucial for the formation of stable water-in-$CO_2$ microemulsions.

In general, the surfactant can be a non-ionic surfactant, such as a fatty molecule (e.g., a fatty alcohol, a fatty acid) or a derivized fatty molecule (e.g., a derivatized fatty alcohol or a derivatized fatty acid). As used herein, a derivatized fatty molecule is a fatty molecule that has been reacted with at least one other compound. For example, the derivatized fatty molecule, in one embodiment, can be alkoxylated to form an alkoxylated fatty molecule. Additionally, for instance, the alkoxylated fatty molecule can be further reacted with a phosphoric compound, such as phosphorous pentoxide, polyphosphoric acid, or the like.

In one embodiment, the surfactant of the present invention can comprise a derivatized fatty alcohol. Fatty alcohols are long chain alcohols typically having the formula of

R—OH wherein R represents a hydrocarbon chain, either saturated or unsaturated. The hydrocarbon chain of the fatty alcohol can be of any length, such as comprising from about 6 to about 26 carbons, for example from about 8 to about 22 carbons. For instance, in one particular embodiment, the hydrocarbon chain can comprise from about 10 carbons to about 14 carbons.

The hydrocarbon chain on the derivatized fatty alcohol surfactant can be either saturated or unsaturated fatty alcohols, including both monounsaturated and polyunsaturated fatty alcohols. A saturated carbon chain means that all the carbon to carbon bonds in the hydrocarbon chain are single bonds, allowing the maximum number of hydrogens to bond to each carbon, thus the chain is "saturated" with hydrogen atoms. Conversely, an unsaturated hydrocarbon chain means that the carbon chain contains at least one carbon to carbon double bond, thereby reducing the number of hydrogens present on the chain. A monounsaturated hydrocarbon chain contains one carbon to carbon double bond, while a polyunsaturated hydrocarbon chain contains at least two carbon to carbon double bonds.

Many fatty alcohols have common names, relating to their corresponding hydrocarbon chain, to describe the alcohol. The hydrocarbon chains can also be described by the number of carbon atoms present in the chain and the number and location of any double bonds present in the chain, represented by $n{:}m^{\Delta p,p',p''}$, where n is the number of carbons in the hydrocarbon chain, m is the number of carbon to carbon double bonds in the chain, p is the location of the first double bond (if present), p' is the location of the second double bond (if present), p" is the location of the third double bond (if present), and so on. Examples of saturated fatty alcohols that can be used as an surfactant include, but are not limited to, lauryl alcohol (12:0), tridecyl alcohol (13:0), myristil alcohol (14:0), pentadecyl alcohol (15:0), cetyl alcohol (16:0, also known as palmityl alcohol), heptadecyl alcohol (17:0), stearyl alcohol (18:0), arachidyl alcohol (20:0), and behenyl alcohol (22:0). Examples of unsaturated fatty alcohols that can be used as an surfactant include, but are not limited to, palmitoleyl alcohol ($16{:}1^{\Delta 9}$), oleyl alcohol ($18{:}1^{\Delta 9}$), linoleyl alcohol ($18,2^{\Delta 9,12}$), conjugated linoleyl alcohol ($18{:}2^{\Delta 9,11}$), linolenyl alcohol ($18{:}3^{\Delta 9,12,15}$), γ-linolenyl alcohol ($18{:}3^{\Delta 6,9,12}$), eicosenoyl alcohol (20:1), eicosadienoyl alcohol ($20{:}2^{\Delta 11,14}$), arachidonyl alcohol ($20{:}4^{\Delta 5,8,11,14}$), cetoleyl alcohol ($22{:}1^{\Delta 11}$), and erucyl alcohol ($22{:}1^{\Delta 13}$).

Derivatives of unsaturated fatty alcohols can also be used as surfactants according to the present disclosure. For example, the hydrocarbon chain of the fatty molecule can comprise a reactive group. For instance, the hydrocarbon chain can comprise an acrylate group.

In one embodiment, the surfactant of the present disclosure can be a derivative of a fatty alcohol. For example, a fatty alcohol as described above can be alkoxylated to form an alkoxylated fatty alcohol, also known as an alcohol alkoxylate. Such as, in one embodiment, the fatty alcohol can be ethoxylated to form an ethoxylated fatty alcohol, also known as an alcohol ethoxylate. For example, the fatty alcohol can be reacted with from 1 mole to about 10 moles of ethylene oxide, such as from about 2 to about 8 moles. The resulting product of the fatty alcohol ethoxylation can generally be represented by the following formula:

$$R—O—(CH_2CH_2O—)_nH$$

where R is the carbon chain of the fatty alcohol and n is an integer from 1 to about 10, such as from about 2 to about 8. In one particular embodiment, for example, n can be about 6. Another suitable alkoxylated fatty alcohol can be propoxylated by reacting propylene oxide with the fatty alcohol to form an propoxylated fatty alcohol, also known as an alcohol propoxylate. For example, the fatty alcohol can be reacted with from 1 mole to about 10 moles of propylene oxide, such as from about 2 to about 8 moles.

In another embodiment of the present invention, the surfactant can comprise a derivatized fatty acid. Fatty acids have a similar structure to fatty alcohols described above and can be represented by the following formula: RCOOH where R represents a hydrocarbon chain, either saturated or unsaturated. In this embodiment, the fatty acid surfactants can have the same hydrocarbon chains as described above in reference to fatty alcohols. Also, as described above, fatty acids can be saturated, monounsaturated, or polyunsaturated. In one particular embodiment, the fatty acid can be comprise a conjugated hydrocarbon chain. Many fatty acids have common names, relating to their hydrocarbon chain, that describe the molecule. In fact, most the fatty alcohols listed above, either saturated or unsaturated, have a corresponding fatty acid molecule with a similar common name. Those corresponding fatty acids are included, as well as others, within the scope of this disclosure.

Also, in this embodiment, the fatty acid can be derivatized by alkoxylation as described above in reference to the derivatized fatty alcohol embodiment.

In yet another embodiment, the derivatized fatty molecule, such as a derivatized fatty alcohol or a derivatized fatty acid, can be alkoxylated with a combination of alkylene oxides. For example, the derivatized fatty molecule can include at least one ethylene ester and at least one propylene ester, as represented below:

$$R—O—(CH_2CH_2O—)_n—(CH_2(CH_3)CH_2O—)_m—H$$

where n is about 1 to about 8 and m is about 1 to about 8. One particularly suitable surfactant is available commercially under the trade name Dehypon Ls-54 from Cognis Corporation, now part of BASF, which is believed to be a fatty alcohol (C12-C14) with approximately 5 moles ethylene oxide and approximately 4 moles propylene oxide (i.e., where R includes a fatty alcohol (i.e., R is R—CO—), n is about 5, and in is about 4). The reason for high solubility may be that the Ls-54 surfactant has low molecular weight and has four propylene oxide groups, which have been proven to be $CO_2$-philic, Fluorosurfactants are also compatible with $CO_2$, and can include the class of alkane/fluoroalkane hybrids and perfluoropolypropylene oxide (e.g., fluorinated sodium bis(2-ethylhexyl)sulfosuccinate (AOT) analogue). The fluorinated chains represent low cohesive energy density groups thereby promoting low solubility parameters and low polarizability. Although high $CO_2$ compatibility can be achieved by fluorinated surfactants, the cost of fluorinated compounds is high and they are toxic. On consideration of the environmental and economical factors, hydrocarbon surfactants, hybrid fluorocarbon-hydrocarbon surfactants, and oxygen-containing surfactants formed by incorporating oxygen into the surfactant tails may be more suitable for use. Another specific example of an oxygen-containing surfactant (other than Ls-54) is octa (ethylene glycol) 2,6,8-trimethyl-4-nonyl ether. Other oxygenated surfactants include nonionic block copolymers composed of oligomers of propylene oxide or butylene oxide with branches on the polymer backbone.

$CO_2$ has relatively low interfacial tension, liquid-like solvating properties, and gas-like diffusion and viscosity that enable rapid penetration into complex structures for the removal of contaminants. The unique properties of compressed $CO_2$, coupled with those of a dispersed microemulsion phase, enables dissolution of the endotoxins and subsequently, removal from the contaminated metallic parts. Thus, such a method can out-perform traditional water-based cleaning processes, particularly for complex structures, since it is not be hampered by high surface tensions as occurs with water.

Thus, in one particular embodiment, the compressed $CO_2$-based mixtures include carbon dioxide, a surfactant, and water in the form of water-in-$CO_2$ microemulsions. In one particular embodiment, the compressed $CO_2$-based mixture can be substantially free from other components (i.e., consisting essentially of carbon dioxide, a surfactant, and water in the form of water-in-$CO_2$ microemulsions). When the surfactant mixture is applied, the contaminant (e.g., the endotoxin) becomes dissolved in the water inside the microemulsion. So, any contaminant may be incorporated or dissolved inside the surfactant structure.

The concentration of $CO_2$ itself is not meaningful, since there is an array of tiny droplets floating in a vast excess amount of $CO_2$. What is critical is the range of ratios of water-to-surfactant that are mixed together in the $CO_2$. This ratio, referred to as "$W_0$", can have a range of about 5-100 molecules of water per molecule of surfactant (e.g., about 5-30 molecules of water per molecule of surfactant).

The compressed $CO_2$-based mixture generally has a pressure of at least about 400 psi (e.g., nominally about 400 to about 600 psi). However, in certain industrial applications, the compressed $CO_2$-based mixture can have a pressure of about 800 to about 5000 psi. Thus, in order to apply the compressed $CO_2$-based mixture to the substrate (e.g., a medical device) for removal of any endotoxins, the substrate can be loaded into a chamber, and the compressed $CO_2$-based mixture can be introduced into or formed within the chamber.

EXAMPLES

The purpose of the following illustrative example was to evaluate compressed carbon dioxide ($CO_2$)-based mixtures for the removal of *Escherichia coli* endotoxin first from smooth Ti surfaces and then from more complex geometries such as stainless steel lumens. Both Ti and stainless steel are common medical materials used in many applications that offer relatively high surface energies (33 and 70 mJ/$m^2$, respectively.), which favor endotoxin adherence. Naturally occurring *E. coli* endotoxin was used as the bio-contaminant because it is representative of the endotoxin type commonly found on Ti implant surfaces, catheters, wound dressings, and prosthodontic materials.

Solubilities of Ls-54 surfactant in supercritical (SC) $CO_2$ have been previously measured, and reported to be 0.05 M solubility of Ls-54 in $CO_2$ at 308.15 K and 22.0 MPa, along with a variety of molar water to surfactant ratios ($W_0$) for microemulsion formation at different pressures and temperatures. In this example, $W_0$ was selected to be 12.3 as the appropriate typical but not exclusive composition for our conditions. Thus, the amount of water and surfactant could be calculated based on the volume of the cleaning vessel. Below is a representation of the Ls-54 surfactant chemical structure.

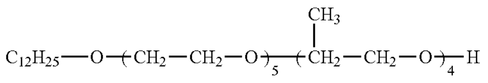

Ls-54

Materials

Chemicals and bio-contaminant. Dehypon Ls-54 surfactant was donated by Cognis Corporation, Ambler, Pa.; and bone-dry grade $CO_2$ (National Welders Supply Co., Durham, N.C.) with 99.8% purity was used as the main cleaning solvent. *E. coli* O55:B5 endotoxin (Lonza Walkersville Inc., Walkersville, Md.) was selected as the model bio-contaminant. Endotoxin-free water (HyPure™ Cell Culture Grade Water) was used for reconstitution, endotoxin recovery, and dilution processes (HyClone Laboratories Inc., Logan, Utah). The Limulus Amebocyte Lysate (LAL) Kinetic-QCL assay kit (Lonza Walkersville Inc.) was employed to determine endotoxin levels.

Substrates. Commercially pure Ti disks with smooth surfaces measuring 12 mm in diameter and 2.5 mm in thickness were provided by Dr. Yuehuei An of the Medical University of South Carolina. Stainless steel tubes (Valco Instruments Co. Inc., Houston Tex.) of 3.175 mm (⅛ in) OD and 2.159 mm (0.085 in) ID were used to simulate lumens. Lengths of 102 mm (4 in) and 610 mm (24 in) were used to study the effect of length on cleaning efficiency.

Methods

Disk Surface Preparation. Disk surfaces were polished using sand paper (40, 15, 9, 5, and 1 μm grit) in a Multiprep polisher (Allied High Tech Products Inc., Rancho Dominguez, Calif.) for 20 minutes per grit. Subsequently, the disks were passivated using ASTM Standard F86-76. This standard requires sonication (Bransonic Ultrasonic Cleaner, model 8510R-MT, Branson Ultrasonics Corporation) in a detergent solution for 15 minutes, then acetone for 15 minutes and finally in 30% nitric acid for 30 minutes. After each step the disks were rinsed three times with DI water.

Depyrogenation of Materials. Before each experiment, Ti disks, lumens, pipettes, and other glassware were depyrogenated in a dry heat oven (Fisher Scientific Isotemp Oven, model 725F) at 250° C. for 30 minutes. For depyrogenation, pipettes were placed in metal canisters and beakers, bottles, and disks were wrapped in aluminum foil. The LAL assay indicated no endotoxin on the depyrogenated items after evaluation.

Endotoxin Reconstitution and Stock Solution Preparation. Vials of lyophilized *E. coli* endotoxin (2.5 mg/vial; nominal $7.5\times10^6$ EU) were reconstituted as specified by the supplier and diluted with endotoxin-free water to obtain multiple stock solution concentrations. Subsequently, the desired substrate was contaminated using the stock solution.

Endotoxin Detection Assay. Endotoxin levels were assayed using the chromogenic LAL Kinetic-QCL assay, which has a sensitivity range of 0.005-50 EU/mL. Samples were placed in a multi-detection microplate reader (model Synergy HT, Bio-Tek Instruments, Inc., Winooski, Vt.) and incubated for 10 minutes at 37° C. After the initial incubation, the LAL reagent was added and the samples were automatically monitored over time at 405 nm throughout the incubation period. The reaction time is inversely proportional to the endotoxin level. The concentration of endotoxin in a given sample is then calculated from the reaction time by comparison to the reaction time of solutions containing known amounts of endotoxin standard.

Figure 2:
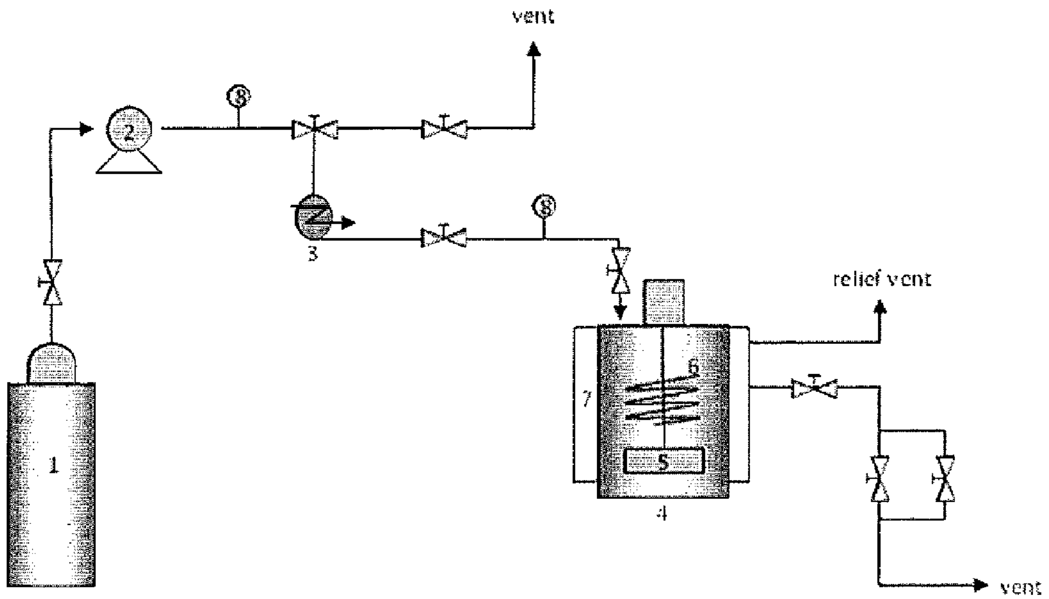
FIG. 2 shows a schematic of the 1 L pressure vessel apparatus according to the Examples, in which the following components are shown: (1) $CO_2$ gas cylinder; (2) pump; (3) water/coolant bath; (4) pressure vessel; (5) stainless steel plate attached to the shaft; (6) cooling coil; (7) heating jacket; (8) pressure indicators.

Procedure for Coating and Processing Ti Disks. An aliquot of 200 μL from a stock solution of approximately 12,000 EU/mL was applied on the Ti disk surface and dried in a biohood at room temperature. This produced a film of approximately 2,000-2,500 EU/disk, depending on the stock solution concentration. Three coated disks 12 and one non-coated disk 14 were secured in a stainless steel plate 10 as shown in FIG. 1. The plate 10 was then attached to the shaft 16 of a stirrer and placed in a 1 L pressure vessel (FC series, Pressure Products Industries, Warminster, Pa.) for processing. A schematic of the 1 L pressure vessel apparatus is shown in FIG. 2. A standard $CO_2$ gas cylinder 1 provides $CO_2$ to the pump 2 (model P, Thar Design Inc., Pittsburgh Pa.), which in turn delivers compressed $CO_2$ to the vessel 4. An external heating jacket 7 and internal cooling coil 6 are provided at the vessel 4 to maintain the desired temperature. The shaft 16 is rotated at 400 rpm, which generates local shear forces on the surface of the disks 12, 14. However, the rotation of the flat disk 5 does not cause significant agitation of $CO_2$ in the vessel. After the desired time, the stirrer motor is turned off and the vessel 4 is depressurized. Temperatures and pressures for this preliminary study ranged from 5 to 40° C. and 13.8 to 27.6 MPa, respectively.

Figure 3:
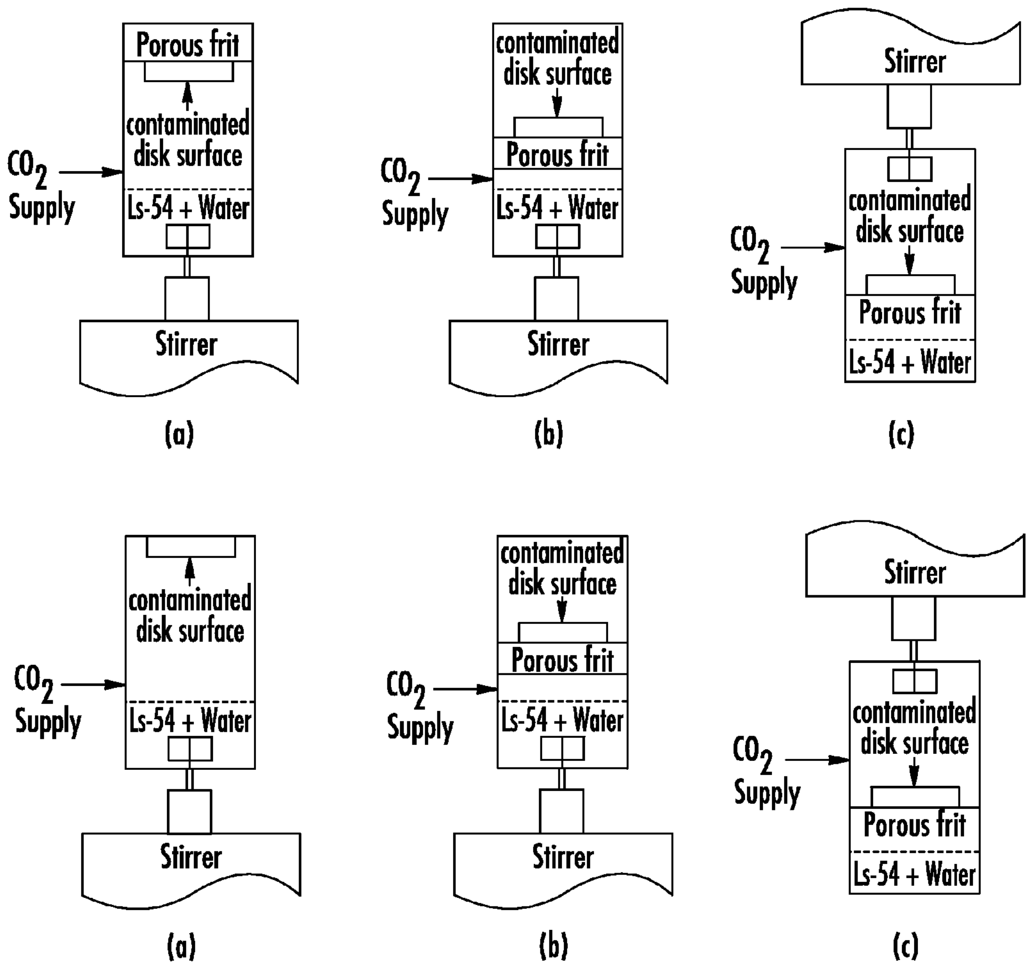
FIG. 3 shows configurations employed within the PEM vessel according to the Examples.

Further experiments were then conducted in a 23 mL phase equilibrium monitor (PEM) vessel (SPM 20, Thar Technologies Inc., Pittsburgh Pa.), which is a high pressure vessel having a maximum volume of 23 mL. A schematic of the apparatus is given in FIG. 3. The PEM is equipped with a video camera and sapphire windows (not shown) to allow visualization of the contents under pressure. It also has a motor-driven stirrer that allows high stirring rates, up to 3,800 rpm. Three physical configurations (as illustrated by FIG. 3) were investigated to study the effects of bulk agitation with and without mass transfer restrictions. All experiments in the PEM vessel were 2 hours long and stirring was set to 1900 rpm. A porous fit (5 μm porous size) is employed to support the disk and prevent initial direct contact between the coated surface and additives (surfactant and water) while the system is set-up. The frit also serves as an internal mass transfer barrier to create the desired flow restrictions for configurations shown in FIGS. 3*b* and 3*c*. Due to the volume limitation in this system, only one disk per experiment was processed at a time. Endotoxin recovery from Ti surfaces was achieved by sonication in an ultrasonic cleaner (model 250D, VWR, West Chester, Pa.). The disks (whether treated or untreated) were placed individually in a 40 mL depyrogenated glass bottle with 20 ml of endotoxin-free water and sonicated for 10 minutes Immediately following the recovery procedure, samples were diluted (1:200) and tested with the LAL assay.

Procedure for Inoculation and Processing Lumens. A stock solution of approximately 30,000 EU/mL was drawn through the length of the lumens with the use of a syringe. The lumens were then capped at one end and placed vertically in a vacuum oven (VWR Vacuum Oven, model 1450M) for approximately 17 hours at 70° C. and 50.5 kPa to evaporate the water, leaving the endotoxin coated to the interior. Lumens were weighed in an analytical balance (model XS105 DualRange, Mettler-Toledo Inc., Columbus Ohio) before and after filling. On average the amount of stock solution was 0.360±0.005 g in the 102 mm lumens and 2.119±0.009 g in the 610 mm lumen. Measurements taken after drying confirmed that the water was completely evaporated. Endotoxin-contaminated lumens were processed for two hours in the same 1 L pressure vessel configuration shown in FIG. 2. Bulk agitation was provided by a flat-blade impeller rotating at 1900 rpm. Endotoxin recovery was carried out by placing the lumens separately in depyrogenated glass containers with an amount of endotoxin-free water (15 mL for the 102 mm lumens and 350 mL for the 610 mm lumen) and sonicated for 10 minutes. Immediately following the endotoxin recovery procedure, samples were diluted (1:200 and 1:100, respectively) and tested for endotoxin levels.

Results and Discussion

Smooth Ti Disks

Initial experiments were carried out in the 1 L pressure vessel with non-bulk agitation in both liquid (5° C.; 13.8 and 27.6 MPa) and supercritical (40° C.; 27.6 MPa) $CO_2$ regions. Table I summarizes conditions (temperature, pressure, and time) and endotoxin loadings evaluated using the 1 L pressure vessel. Subsequent experiments were completed in the PEM vessel to investigate the impact of bulk agitation and mass transfer limitations at the conditions of pressure and temperature that gave the best indication of endotoxin removal in the 1 L pressure vessel.

Figure 4A:
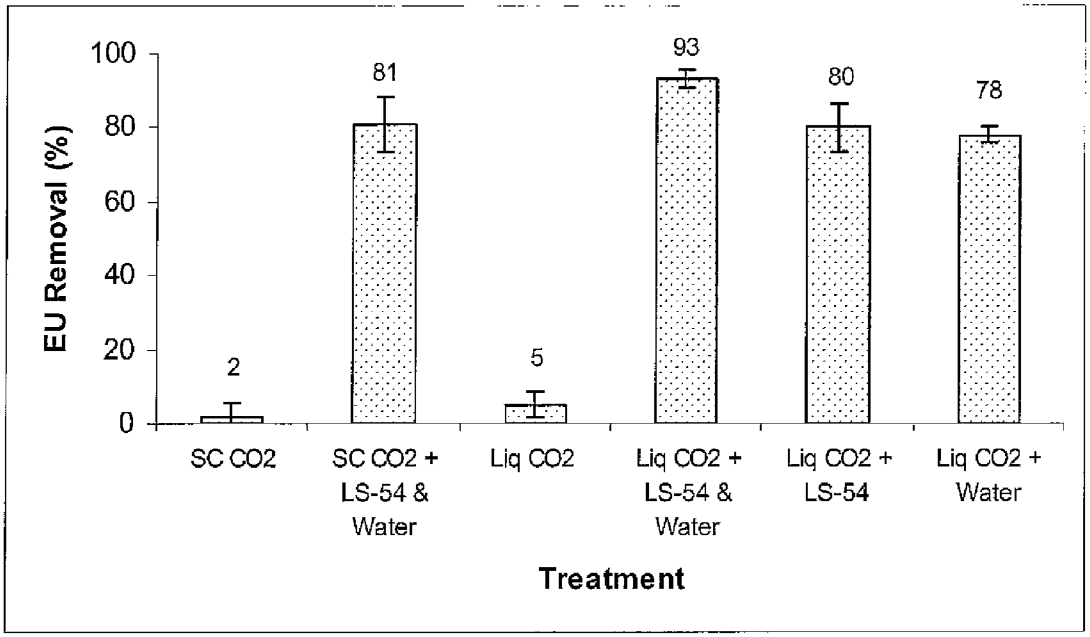
FIG. 4 shows results according to the Examples of processing disks with pure $CO_2$ and $CO_2$-based mixtures in the 1 L pressure vessel: (a) percent of endotoxin removed (Mean±SD); and (b) residual endotoxin levels (Mean±SD).
Figure 4B:
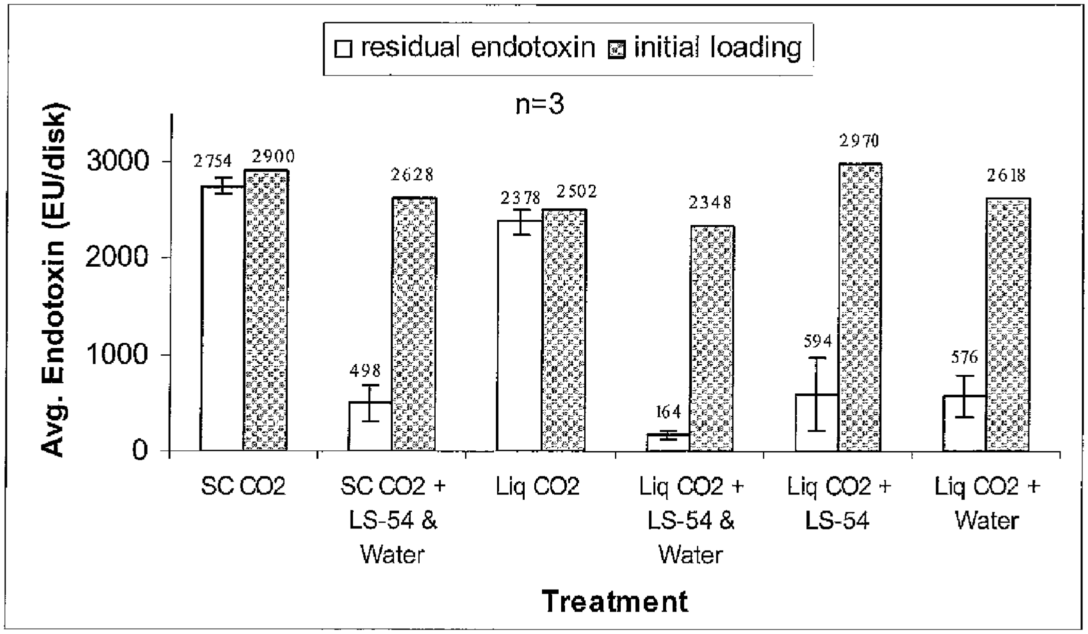

The maximum recoverable endotoxin was defined as the endotoxin recovered from a contaminated, untreated disk immersed and sonicated in endotoxin-free water (negative controls). Treated disks were compared against the negative controls in each experiment to determine the endotoxin removal level. FIG. 4 shows the percentage endotoxin removal (FIG. 4*a*) and the residual endotoxin levels (FIG. 4*b*) for each treatment in the 1 L pressure vessel at 4 hours and 27.6 MPa. Neither pure SC $CO_2$ nor liquid $CO_2$ removed a significant fraction of endotoxin from the Ti surfaces. This is as expected, because $CO_2$ alone has insufficient solvent strength to dissolve the large endotoxin biomolecule. These results agree with a visual experiment previously performed in the PEM, where it was observed that compressed $CO_2$ did not dissolve endotoxins. For experiments employing liquid $CO_2$+Ls-54 and liquid $CO_2$+water, 80% and 78% endotoxin removal was attained, respectively. However, adding both Ls-54 and water together in $CO_2$ enhanced the removal to 93% as shown in FIG. 4. High levels of endotoxin removal were achieved when adding Ls-54 and water to both SC $CO_2$ (81%) and liquid $CO_2$ (93%). These results suggest that Ls-54 microemulsions are formed in either the liquid or SC $CO_2$ phase and the microemulsion system is effective in removing endotoxins. Nevertheless, microemulsions in liquid $CO_2$ removed a greater fraction of endotoxin than SC $CO_2$ microemulsions. The higher efficiency achieved in the liquid state ($\rho$=23.4 mole/L, 5° C. and 27.6 MPa) suggests that more microemulsions are formed in this state than in the SC state ($\rho$=20.4 mole/L, 40° C. and 27.6 MPa), because Ls-54 has higher solubility in compressed $CO_2$ at lower temperatures and constant pressures according to the data presented by Liu et al. (2002).

The 80% endotoxin removal for experiments with liquid $CO_2$+Ls-54 only, suggests formation of a microemulsion of the surfactant and endotoxin. Thus, indicating that an inverse micelle is still formed between the non-polar solvent and the surfactant allowing the endotoxin removal. However, further phase equilibrium studies should be addressed to evaluate this hypothesis.

Endotoxin removal was also appreciable when processing the Ti disks with liquid $CO_2$+water (78% endotoxin removal). Both the effect of water in the solvent capability of $CO_2$ and its affinity for endotoxins are to be examined. According to King et al. (1992) the water solubility in $CO_2$ at 25° C. and 20.7 MPa is approximately 0.079 M. Hence, for experiments carried out in the 1 L pressure vessel having $CO_2$+water, it is expected that at least 1.4 mL of water (out of the 12 mL initially added) is dissolved in $CO_2$. It is thus believed that water might work as a co-solvent, as previously reported by Casas et al. (2007) for the extraction of bioactive compounds using SC $CO_2$, increasing its polarity to enhance the endotoxin removal. In addition, LPS molecules contain long carbohydrate chains that favor its solubility in water. The LPS molecule contains two regions; the lipid chain (Lipid A) that is the hydrophobic region and the polysaccharide section (O-antigen and Core Region) that maintains the hydrophilic domain of the molecule. This suggests that the hydrophilic group in the endotoxin (which is larger than the hydrophobic region) dissolves in the mixture of liquid $CO_2$+water, thus explaining its removal.

Liquid and SC $CO_2$ microemulsions decreased the endotoxin levels in the disks to 144 and 498 EU/disk, respectively, from an initial loading of approximately 2,500 EU/disk. It is desirable to reduce endotoxin to less than 20 EU/disk. This might be feasible with a two-stage process. Hence, experiments with lower initial endotoxin loading (440±32 EU/disk) were conducted in the 1 L pressure vessel with liquid $CO_2$ microemulsions (i.e. $CO_2$ and additives at the liquid state). The cleaned disks had an average endotoxin level of 12±21 EU/disk for an average percent removal of 97%. This level is below the established USP requirements for medical devices and suggests that a two-stage process, using liquid $CO_2$ microemulsions with non-bulk agitation, might remove a theoretical 99.5% of endotoxin for surfaces initially coated with 2,500 EU.

Figure 5:
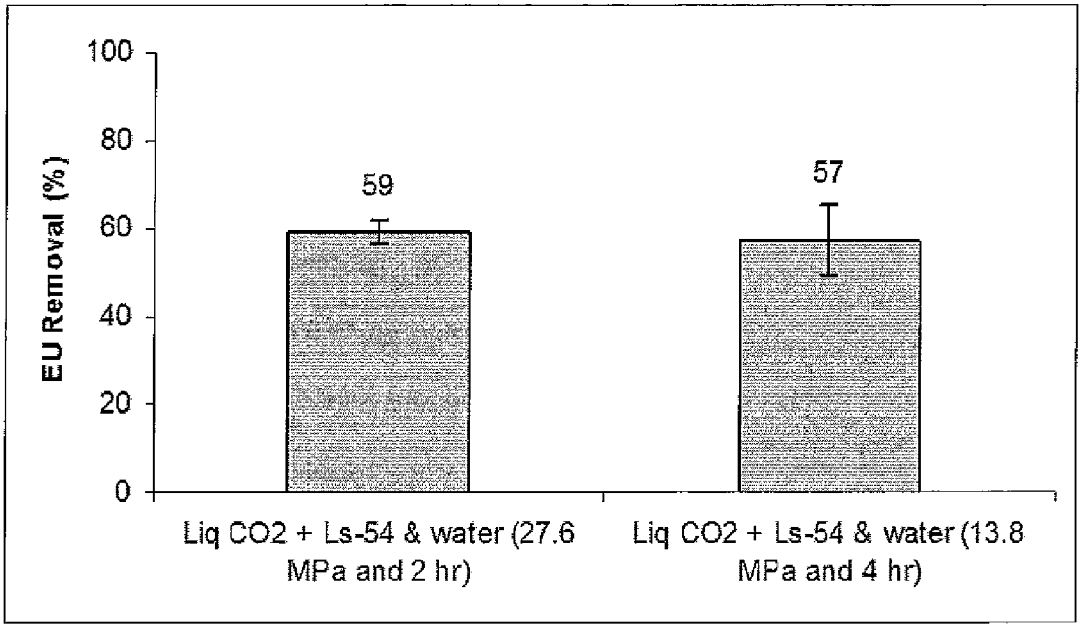
FIG. 5 shows a percent of endotoxin removal (Mean±SD) from Ti disks according to the Examples using liquid $CO_2$+Ls-54 and water at 27.6 MPa & 2 hr; and 13.8 MPa & 4 hr in the 1 L pressure vessel.

The results presented in FIG. 4 were obtained with a 4 hour cleaning at 27.6 MPa. Shorter duration or lower pressures were also evaluated and the results are shown in FIG. 5. The average endotoxin level after 2 hour treatment at 27.6 MPa was 1296±189 EU/disk, corresponding to 59±2.4% removal. For the 4 hour treatment at 13.8 MPa the average endotoxin removal was 57±8%. Both of these treatments were less effective than the 4 hours treatment at 27.6 MPa. According to Liu et al. (2002) the solubility of Ls-54 in $CO_2$ decreases with pressure, thus, one expects less formation of microemulsions. With no bulk mixing in the 1 L pressure vessel, there is a lack of energy to form the microemulsions, thus longer time is needed for the system to reach equilibrium and achieve complete endotoxin removal. Therefore, it is expected that decreasing the duration or pressure of the treatment would reduce the efficiency of endotoxin removal.

Experiments in the PEM vessel were conducted at the temperature and pressure for the highest indication of endotoxin removal determined in the 1 L pressure vessel. Thus, all experiments were conducted in the liquid $CO_2$ region (25° C.; 27.6 MPa), adding either Ls-54 or water or both. The duration of these experiments was 2 hours. Three physical configurations (as shown in FIG. 3) were evaluated and Table II shows the endotoxin loadings and cleaning fluids employed for each configuration.

FIG. 3*a* gives the configuration for endotoxin removal with bulk agitation (1900 rpm stirring rate) and no flow or recirculation restrictions on the $CO_2$/microemulsion fluid. FIGS. 3*b* and 3*c* show two additional configurations of the PEM vessel. These configurations place the porous frit so as to restrict the circulation of the $CO_2$. Thus, it is possible to infer some effects of mass transfer restrictions by comparing results. Configuration 3b simulates of a cleaning process through a porous structure. Configuration 3c is somewhat similar to the 1 L pressure vessel, in that bulk agitation is provided directly to the $CO_2$ but not to the water and surfactant. The main difference between configurations is that 3b allows stirring of all cleaning fluids ($CO_2$ plus additives) while 3c allows stirring only of $CO_2$. For configuration 3b, the cleaning fluids initially lay below the contaminated disk surface, which is on top of the frit.

Figure 6:
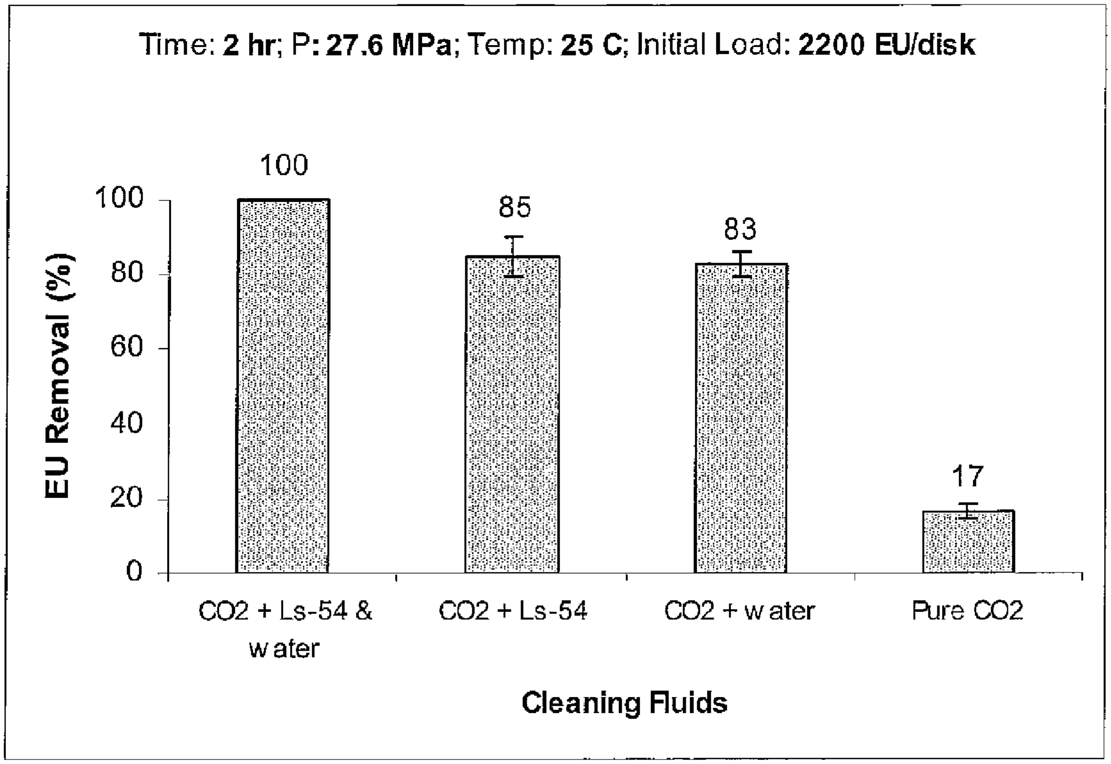
FIG. 6 shows a percent of endotoxin removal (Mean±SD) with liquid $CO_2$ and mixtures of water and Ls-54 in the PEM system, configuration 3a, according to the Examples.

FIG. 6 shows percentage endotoxin removal in the PEM vessel system using configuration shown in FIG. 3*a*. Complete endotoxin removal (100%) was attained with both Ls-54 and water added. With vigorous bulk agitation conditions, the water-in-$CO_2$ microemulsion system is developed rapidly. Stronger agitation will also facilitate the mass transfer of the endotoxin into the microemulsion, making possible its complete removal in 2 hours. When Ls-54 or water were added individually to $CO_2$, the endotoxin removal was similar to that seen in the 1 L pressure vessel. With liquid $CO_2$+Ls-54, 85% of the endotoxin was removed while 83% was removed with liquid $CO_2$+water. However, the cleaning process in the PEM vessel was run for 2 hours at room temperatures (25° C.). This indicates that better (in the case of liquid $CO_2$ microemulsions) or similar (in the case of adding water or Ls-54 individually) endotoxin removal can be achieved in less time when strong stilling is provided. The 17% endotoxin removal with pure $CO_2$ is probably due to higher agitation and physical dislodgment, and residual water from the inlet and outlet lines.

Figure 7:
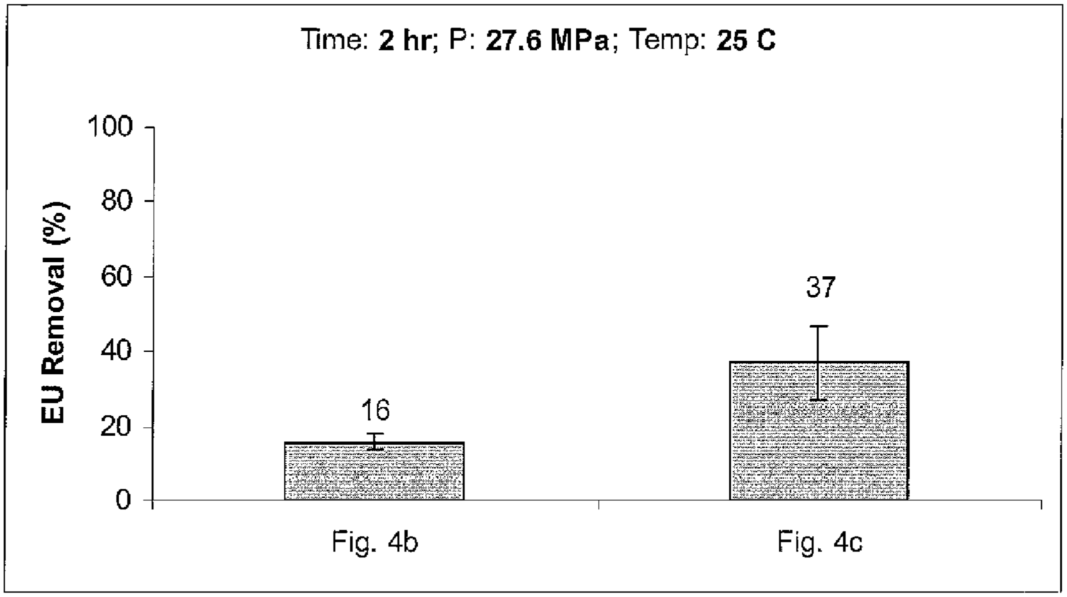
FIG. 7 shows a percent of endotoxin removal (Mean±SD) from Ti disks using liquid $CO_2$+Ls-54 and water in the PEM system with mass transfer limitations and flow restrictions, according to the Examples.

FIG. 7 presents the results for experiments with mass transfer and flow restrictions. For configuration 3b, the average endotoxin removal was only 16%. In this configuration the porous frit initially separates the liquid additives from the contaminated disk. Hence, it is necessary that the water-in-$CO_2$ microemulsion phase migrates through the porous frit to dissolve and remove endotoxin from the disk surface, as would happen in a porous device. Configuration 3b models an actual porous structure where the liquid $CO_2$ microemulsions would be required to penetrate the porous surface in order to remove the contaminant. Because of this restriction, there is a mass transfer limitation and additional time is required to achieve complete endotoxin removal.

For configuration 3c the average endotoxin removal was 37%. In this configuration the liquid $CO_2$ is initially separated from the Ls-54 and water by the porous frit. Agitation is applied to the contaminated surface where liquid $CO_2$ is introduced. Because the contaminated surface is directly exposed to the rotating impeller, it can be inferred that some of the endotoxin removal is due to the high agitation and physical dislodgment. Surfactant and water must diffuse through the porous frit to the contaminated surface for complete removal. A similar phenomenon affected experiments carried out in the 1 L pressure vessel, where limited stirring energy meant that micelles moved to the disk surface mostly by diffusion.

Although strong stirring was provided for configurations 3b and 3c, mass transfer limitation still existed due to the porous frit. Placing the frit to support the disk in the middle of the vessel creates a barrier through which the cleaning fluids must diffuse. The data indicate that removal is dependent on the formation of microemulsion and its diffusion to the contaminated surface. In configuration 3b the microemulsion forms, but there is a diffusion limitation due to the frit barrier. Configuration 3b is more likely to occur in actual cleaning processes; therefore further work should be addressed in this scenario. Configuration 3c has both diffusion and microemulsion formation limitations. This might require more time to allow microemulsion to reach equilibrium and achieve higher removal. In contrast, for configuration 3a, there was neither diffusion limitation nor restrictions.

To take into account any endotoxin re-deposition during depressurization, a blank (non-coated) disk was processed simultaneously along with the contaminated disks for all cleaning trials in the 1 L pressure vessel. For the PEM vessel, due to space limitations, a blank disk was not processed simultaneously with the contaminated substrate. Instead, a non-coated disk was processed separately adding to the cleaning fluids the same amount of stock solution used to coat the disks. None of them exhibited endotoxin contamination when analyzed.

Stainless Steel Lumens

In this study, stainless steel lumens of two different lengths were used to determine whether endotoxin removal could be accomplished. The 102 mm lumens were first used to evaluate the effectiveness of the $CO_2$-based cleaning. Subsequent experiments were then conducted with 610 mm lumens, which are more representative of actual medical applications. Experiments were carried out in the liquid $CO_2$ region (27.6 MPa and 25° C.) employing either pure $CO_2$ or $CO_2$ with surfactant+water as the cleaning fluids.

As in the Ti disks, the maximum recoverable endotoxin for each evaluated lumen was defined as the endotoxin recovered by sonication of the contaminated, untreated lumen (negative control). Endotoxin levels detected from the processed or treated lumen were then compared to the average negative control to determine the endotoxin removal. For the 102 mm length, a total of 3 lumens were used through out the study. The 3 lumens were inoculated and processed simultaneously. On average 4274±682, 4154±398, and 4345±546 EU (n=3) was recovered from each untreated lumen as shown in Table III. Due to space limitations in the pressure vessel, only one lumen was used for the 610 mm length. The average endotoxin recovered from the inoculated, untreated 610 mm lumen was 26,932 EU±4802 (n=3). It needs to be pointed out that the loading in the longer lumen is 204 times greater than the highest endotoxin amount found in reusable angiographic catheters (450-1100 mm in length) as reported by Kundsin and Walter (1980). The high endotoxin loading, along with the fact that stainless steel supports endotoxin adherence, presents a strong cleaning challenge.

Figure 8:
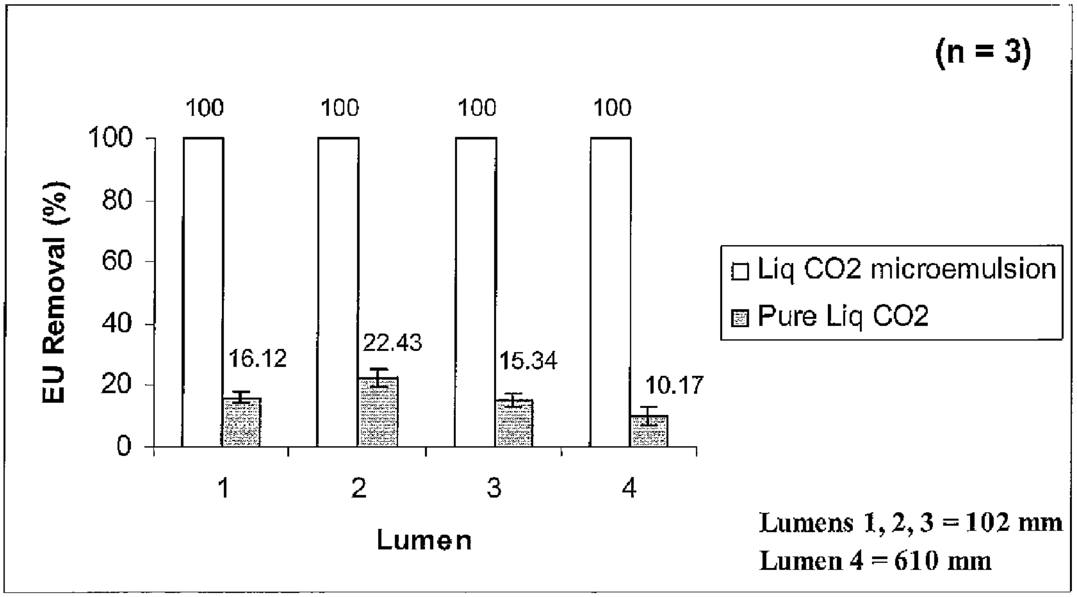
FIG. 8 shows a percent of endotoxin removed (Mean±SD) from stainless steel lumens after processing with pure liquid $CO_2$ and liquid $CO_2$ microemulsions according to the Examples.

FIG. 8 shows the percentage endotoxin removal for all the evaluated lumens after treatment with both liquid $CO_2$ microemulsions and pure liquid $CO_2$. Complete endotoxin removal (100%) was attained for all lumens with liquid $CO_2$ microemulsions. These results, particularly for the long lumen, suggest that there was no mass transfer limitation under the experimental conditions tested in this work. However, pure liquid $CO_2$ did not remove a significant fraction of endotoxin from the stainless steel lumens, as expected. On average the remained EU for each lumen of 102 mm length after pure liquid $CO_2$ treatment was 3585±61, 3222±99, and 3678±84. For the 602 mm length, an average residual endotoxin of 24,254±760 EU remained after pure $CO_2$ treatment. The low removal percentage is consistent with the endotoxin removal attained from smooth Ti surfaces when only pure $CO_2$ is used.

These results are very promising for actual processes dealing with difficult-to-clean long narrow-lumen medical devices. As the design of new biomaterials and medical devices becomes more complex and environmentally-sensitive, new techniques to assure proper endotoxin removal must be developed as well. However, while this study was intended to determine the general efficiency and applicability of this technology, additional work should be addressed for configurations as described by FIG. 3*b*. This configuration presents limitations that could be found in actual cleaning process and also will be representative of porous devices such as those found in acetabular shells and femoral stems. Further work is being conducted applying this technology for porous coated Ti substrates.

Tables:

TABLE I

Experiments in the 1 L Pressure Vessel

| Cleaning Fluid (s) | T (C) | P(MPa) | Time (hr) | Initial loading (EU/disk) |
|---|---|---|---|---|
| Supercritical (SC) $CO_2$ | 40 | 27.6 | 4 | 2900 |
| SC $CO_2$ + Ls-54 & water | 40 | 27.6 | 4 | 2628 |
| liquid $CO_2$ | 5 | 27.6 | 4 | 2502 ± 71 |
| liquid $CO_2$ + Ls-54 & water | 5 | 27.6 | 4 | 2348 ± 82 |
| liquid $CO_2$ + Ls-54 & water | 5 | 27.6 | 4 | 440 ± 32 |
| liquid $CO_2$ + Ls-54 | 5 | 27.6 | 4 | 2970 ± 457 |
| liquid $CO_2$ + water | 5 | 27.6 | 4 | 2618 ± 265 |
| liquid $CO_2$ + Ls-54 & water | 5 | 13.8 | 4 | 2169 ± 810 |
| liquid $CO_2$ + Ls-54 & water | 5 | 27.6 | 2 | 3145 ± 438 |

TABLE II

Experiments in the PEM (25° C., 27.6 MPa, and 2 hrs)

| Cleaning Fluid (s) | Loading (EU/disk) | PEM Configuration |
|---|---|---|
| liquid $CO_2$ + Ls-54 & water | 1633 ± 91 | FIG. 3a |
| Pure liquid $CO_2$ | 2225 ± 85 | FIG. 3a |
| liquid $CO_2$ + Ls-54 | 2225 ± 85 | FIG. 3a |
| liquid $CO_2$ + water | 2225 ± 85 | FIG. 3a |
| liquid $CO_2$ + Ls-54 & water | 1600 ± 100 | FIG. 3b |
| liquid $CO_2$ + Ls-54 & water | 3397 ± 92 | FIG. 3c |

TABLE III

Endotoxin Levels Recovered from Untreated Lumens (102 mm long)

| | Recovered Endotoxin Units (EU) per Lumen | | | |
|---|---|---|---|---|
| Lumen | Exp 1 | Exp 2 | Exp 3 | Mean ± SD |
| 1 | 5007 | 3658 | 4156 | 4274 ± 682 |
| 2 | 4508 | 3723 | 4231 | 4154 ± 398 |
| 3 | 4900 | 3808 | 4327 | 4345 ± 546 |

Conclusions

The presence of endotoxin contamination represents a serious threat to biomaterials and medical products. The present study demonstrated that for a well mixed system, the novel water-in-$CO_2$ microemulsion system described in this invention can, at room temperatures and moderate pressures (25° C. and 27.6 MPa), remove 100% of the endotoxin applied on Ti surfaces and also to the endotoxin inoculated in two different lengths of stainless steel lumens.

Unexpectedly, higher endotoxin removal was achieved in the liquid region (5-25° C. and 27.6 Mpa) than in the SC region (40° C. and 4000 psi). This suggests that water-in-$CO_2$ microemulsions were formed in the liquid region. Higher Ls-54 solubility in compressed $CO_2$ at lower temperatures is shown in the data published by Liu et al (2002).

In the absence of high stirring rates (i.e. poor circulation rates or non-bulk agitation) mass transfer limitation existed; demanding more time for the mixture to reach equilibrium and achieve higher endotoxin removal from the Ti disks.

Safe endotoxin levels (≤20 EU/device as required for medical devices), were achieved after two hours when processing both Ti disks and lumens in a well mixed solution of liquid $CO_2$ microemulsion. At poorly mixed conditions, longer periods of time (>4 hours) were required to attain ≤20 EU/disk.

High fractions of endotoxin were removed from the Ti disks when employing mixtures of liquid $CO_2$ with either water or Ls-54. The endotoxin removal for both treatments was similar and ranged from 80% to 85%. Pure $CO_2$, either in the liquid or SC region, did not remove significant amount of endotoxins from the Ti disks and lumens because they are not soluble in $CO_2$.

The successful removal of endotoxins with compressed $CO_2$ is a promising alternative technology for the final cleaning of biomaterials and reusable medical devices. Compressed $CO_2$ at room temperature and relatively low pressure (25° C. and 27.6 MPa) with a small fraction of Ls-54 surfactant and water completely removed endotoxins from smooth Ti surfaces and stainless steel lumens. The use of $CO_2$ is favorable because $CO_2$ is inexpensive, non-toxic, non-flammable, and is readily available from industrial sources. In addition to complete removal of persistent contaminants such as endotoxins, this technology provides waste minimization and hazardous solvent elimination. The use of $CO_2$ as a cleaning solvent can reduce the need for washing in organic solvents, thus reducing their overall use in manufacturing processes.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of cleaning a medical device, the method comprising loading the medical device into a chamber, and exposing the medical device to a compressed $CO_2$-based mixture within the chamber, the compressed $CO_2$-based mixture comprising carbon dioxide, a surfactant, and water in the form of water-in-$CO_2$ microemulsions, wherein the compressed $CO_2$-based mixture has a pressure of at least 400 psi.

2. The method as in claim 1, wherein the compressed $CO_2$-based mixture consists essentially of carbon dioxide, a surfactant, and water in the form of water-in-$CO_2$ microemulsions.

3. The method as in claim 1, wherein the ratio of water-to-surfactant mixed together in the $CO_2$ has a range of about 5-100 molecules of water per molecule of surfactant.

4. The method as in claim 1, wherein the ratio of water-to-surfactant mixed together in the $CO_2$ has a range of about 5-30 molecules of water per molecule of surfactant.

5. The method as in claim 1, wherein the compressed $CO_2$-based mixture has a temperature of about 0° to about 100° C.

6. The method as in claim 1, wherein the compressed $CO_2$-based mixture has a temperature of about 20° C. to about 60° C.

7. The method as in claim 1, wherein the surfactant is a non-ionic surfactant.

8. The method as in claim 1, wherein the surfactant comprises fatty molecule.

9. The method as in claim 8, wherein the surfactant comprises a derivized fatty molecule.

10. The method as in claim 9, wherein the surfactant comprises a fatty molecule derivatized by alkoxylation.

11. The method as in claim 9, wherein the surfactant comprises a fatty molecule derivatized by fluorination.

12. The method as in claim 1, wherein the compressed $CO_2$-based mixture has a pressure of about 400 to about 600 psi.

13. The method as in claim 1, wherein the compressed $CO_2$-based mixture has a pressure of about 800 to about 5000 psi.

14. The method as in claim 1, wherein the compressed $CO_2$-based mixture is a liquid.

15. The method as in claim 1, wherein the compressed $CO_2$-based mixture is a super critical fluid.

16. The method as in claim 1, wherein the compressed $CO_2$-based mixture removes at least about 85% of bacterial endotoxin from the medical device.

17. The method as in claim 1, wherein the compressed $CO_2$-based mixture removes at least about 95% of bacterial endotoxin from the medical device.

18. The method as in claim 1, wherein the compressed $CO_2$-based mixture removes at least about 99% of bacterial endotoxin from the medical device.

19. The method as in claim 1, wherein exposing the exposing the medical device to a compressed $CO_2$-based mixture within the chamber comprising introducing the compressed $CO_2$-based mixture into the chamber.

20. The method as in claim 1, wherein exposing the medical device to a compressed $CO_2$-based mixture within the chamber comprises forming the compressed $CO_2$-based mixture within the chamber.

* * * * *